United States Patent
Zardi (12) 
(10) Patent No.: US 7,109,301 B1
(45) Date of Patent: Sep. 19, 2006

(54) TENASCIN-C ISOFORM AS MARKER FOR NEOPLASIAS

(75) Inventor: Luciano Zardi, Recco (IT)

(73) Assignee: Philogen S.p.A., Siena (IT)

( * ) Notice: Subject to any disclaimer, the term of this patent is extended or adjusted under 35 U.S.C. 154(b) by 0 days.

(21) Appl. No.: 09/959,373

(22) PCT Filed: Apr. 19, 2000

(86) PCT No.: PCT/EP00/03550

§ 371 (c)(1),
(2), (4) Date: Oct. 18, 2001

(87) PCT Pub. No.: WO00/63699

PCT Pub. Date: Oct. 26, 2000

(30) Foreign Application Priority Data

Apr. 20, 1999 (IT) ................................ FI99A0094

(51) Int. Cl.
*C12P 21/08* (2006.01)
*C07K 16/00* (2006.01)
*C07K 17/00* (2006.01)
*G01N 33/53* (2006.01)
*A61K 39/395* (2006.01)

(52) U.S. Cl. ................ 530/387.1; 530/387.3; 530/387.7; 530/388.1; 530/388.8; 530/388.85; 530/391.1; 530/391.3; 435/7.1; 424/130.1

(58) Field of Classification Search ............. 514/2; 424/130.1; 530/387.1, 387.3, 387.7, 388.1, 530/388.8, 388.85, 391.1, 391.3; 435/7.1
See application file for complete search history.

(56) References Cited

OTHER PUBLICATIONS

Gura (Science, 1997, 278:1041-1042).*
Jain (Sci. Am., 1994, 271:58-65).*
Curti (Crit. Rev. in Oncology/Hematology, 1993, 14-29-39).*
Johnston and Thorpe (Immunochemistry in Practice, Blackwell Scientific Publications, Oxford, 1987, pp. 49-50).*
Meiners et al (J. Neuroscience, 1999, 19:8443-8453).*
Murphy-Ullrich et al (J. Cell. Biol., 1991, 115:1127-1136).*
Klausner,(Biotechnology, 1986, 4:1042-1043).*

* cited by examiner

Primary Examiner—Susan Ungar
(74) Attorney, Agent, or Firm—Abelman, Frayne & Schwab (57) ABSTRACT

Diagnostic method for the identification of human neoplasias based on the determination of the CTN-C isoform of TN-C, fragments antibodies and their conjugates used in said method, and their therapeutic use.

12 Claims, 8 Drawing Sheets

FIGURE 3 (A and B)

FIGURE 3 (C, D, E and G)

FIGURE 4 (A and C) (B and D)

FIGURE 4 (E and F)

TENASCIN-C ISOFORM AS MARKER FOR NEOPLASIAS

FIELD OF THE INVENTION

The present invention refers to a diagnostic method allowing a highly specific identification of human neoplasias by means of fragments of recombinant human antibody, and to said fragments and conjugates thereof. The invention also refers to the use of fragments and conjugates thereof in the preparation of therapeutically useful formulations.

STATE OF THE ART

During neoplastic growth, the extracellular matrix (hereinafter referred to as ECM) of normal tissues, where tumour growth takes place, is remodelled by processes of proteolytic degradation and synthesis of new components.

ECM components of tumors differ from those of normal tissues, in terms of quantity and quality, and contribute to the creation of conditions favoring tumor growth and development, among which is angiogenesis, which plays a major role in neoplastic development.

Tenascin-C (hereinafter referred to as TN-C) is a glycoprotein consisting of six similar subunits linked by disulphide bonds. It is coded for by a single gene and its expression is regulated by a single promoter.

Through a mechanism known as alternative splicing, 9 proteic domains, homologous to the "type III fibronectin domains" (hereinafter referred to as FNIII) can be either included in or omitted from the mRNA of human TN-C, giving rise to various proteic isoforms.

It is also known that TN-C isoforms are abundantly present in normal adult tissues and that TN-C isoforms including most or all 9 domains mentioned above are very widely expressed in neoplastic tissues.

The reagents suitable for identifying TN-C isoforms available to date are murine monoclonal antibodies that, as such, are not appropriate to be used in man (e.g. immunoscintigraphy); furthermore, they react indiscriminately with the isoforms present in neoplastic and healthy tissues.

Therefore, it is clear that it would be of major importance to develop a method and reagents allowing the identification of the isoforms present in neoplastic tissues alone. This, in fact, would permit a highly precise and specific diagnosis, while making it possible for a drug or another effector to reach the tumour only, for therapeutic purposes.

DESCRIPTION OF THE FIGURES

FIG. 1A: Structural model (in domains) of a subunit of human TN-C. Oval and square symbols represent EGF-like and FN-like repeats, respectively. The amino terminal and the fibrinogen-like terminal COOH knob are also shown. FN-like repeats from A1 to D, whose expression is regulated by pre-mRNA alternative splicing, are shaded. The top part of the figure also shows the TN-C-β-galactosidase fusion proteins or recombinant proteins used. Arrows indicate the position of the epitopes of each recombinant or monoclonal antibody. A indicates continuity.

FIG. 1B: Electrophoresis in Sodium Dodecyl Sulphate (4–18% SDS. PAGE) of 'long' recombinant protein TN-C (containing domains A1 to D) and 'short' TN-C (not containing domains A1 to D), stained with Coomassie blue, and immunoblots stained using scFv TN11 and TN12.

FIG. 1C: Immunoblots of various fusion and recombinant proteins (A), stained with scFv TN11 and TN12. The values reported on the left indicate the molecular mass (in kilodaltons) of standards.

FIG. 5: Demonstration by Southern blot of the specificity of the cRNA probe used for in situ hybridisation experiments. Bottom: staining of agarose gel with ethidium bromide. 1: TNFNALL (which comprises the DNA of human TN-C from domain 2, type III to domain 7, type III, including the domains subjected to splicing); 2: TNFN1–8 (the same as the TNFNALL sequence, but without the domains subjected to splicing); 3: all TNEGF-like domains; 4: domain D, type III; 5: domain C, type III; 6: domain 1, type III; 7: TNEGF-like domains from 8 to 10; 8: standard.

Top: Southern blot of the same fragments as described above, hybridised with the DIG-labelled probe. Numbers on the right are measured in kb.

DETAILED DESCRIPTION OF THE INVENTION

It has now been found that human TN-C isoforms containing domain C (hereinafter referred to as cTN-C) are greatly expressed in vascular structures and in proximity of high grade astrocytoma proliferating cells (grade III) and glioblastoma. The isoforms in question are also widely expressed in vascular structures of pulmonary human neoplasia, whereas they are not detected in any normal adult human tissue.

Therefore, the present invention refers to a method for the identification of neoplastic tissues in vivo and in vitro, based on the determination of the presence of the cTN-C isoforms of TN-C.

The invention also refers to ligands capable of recognising cTN-C and conjugates thereof.

The term 'ligands' is used herein to mean antibodies or fragments thereof or any other molecule capable of recognising and binding itself to cTN-C.

In particular, according to the present invention, 'ligands' are fragments of recombinant human antibodies and more particularly scFv fragments. In fact, compared with conventional immunoglobulins, small fragments of human antibodies, as the scFv fragments are, do not accumulate in the liver, are not immunogenic and exhibit a better penetration into tissues.

According to the invention, useful conjugates can be obtained by known techniques by biochemical or genetic conjugation of the ligand for cTN-C to the molecules suitable for the fixed diagnostic and/or therapeutic purpose. Appropriate molecules for the conjugation with the ligand may be, e.g., radioisotopes, fluorescent substances, cytokines, toxins, photosensitizers, thrombogenetic agents, etc.

To construct the conjugates according to the invention it is possible to use, e.g., the ligand described above as well as peptides or other non-proteic molecules. Particularly interesting, according to the invention, is the ligand represented by the recombinant human antibody scFv, whose sequence is reported in Table 1 (SEQ ID NO. 1) hereinafter referred to as TN11.

TABLE 1

TN11 sequence deduced from the DNA sequence

```
1/1                                              31/11
CAG GTG CAG CTG GTG CAG TCT GGG GCT GAG GTG AAG AAG CCT GGG TCC TCG GTG AAG GTC
 Q   V   Q   L   V   Q   S   G   A   E   V   K   K   P   G   S   S   V   K   V

61/21                                            91/31
TCC TGC AAG GCT TCT GGA GGC ACC TTC AGC AGC TAT GCT ATC AGC TGG GTG CGA CAG GCC
 S   C   K   A   S   G   T   F   S   S   Y   A   I   S   W   V   R   Q   A

121/41                                           151/51
CCT GGA CAA GGG CTT GAG TGG ATG GGA GGG ATC ATC CCT ATC TTT GGT AGA GCA AAC TAC
 P   G   Q   G   L   E   W   M   G   G   I   I   P   I   F   G   T   A   N   Y

181/61                                           211/71
GCA CAG AAG TTC CAG GGC AGA GTC ACG ATT ACC GCG GAC GAA TCC ACG AGC ACA GCC TAC
 A   Q   K   F   Q   G   R   V   T   I   T   A   D   E   S   T   S   T   A   Y

241/81                                           271/91
ATG GAG CTG AGC AGC CTG AGA TCT GAG GAC ACG GCC GTG TAT TAC TGT GCG AGA TCG AGA
 M   E   L   S   S   L   R   S   E   D   T   A   V   Y   Y   C   A   R   S   R

301/101                                          331/111
CGT ATT ACG ATT TTT GGA GGA GGT GCT TTC GAT ATC TGG GGC CGA GGC ACC ATG GTC ACC
 R   I   T   I   F   G   G   G   A   F   D   I   W   G   R   G   T   M   V   T

361/121                                          391/131
GTC TCT TCA GGT GGG GGC GGT TCA GGC GGA GGT GGC AGC GGC GGT GGC GGA TCG CAG TCC
 V   S   S   G   G   G   G   S   G   G   G   G   S   G   G   G   G   S   Q   S

421/141                                          451/151
GTG CTG ACT CAG CCT GCC TCC GTG TCT GGG TCT CCT GGA CAG TCG ATC ACC ATC TCG TGC
 V   L   T   Q   P   A   S   V   S   G   S   P   G   Q   S   I   T   I   S   C

481/161                                          511/171
ACT GGA ACC AGC AGT GAT GTT GGT GGT TAT AAC TAT GTC TCC TGG TAC CAA CAA CAC CCA
 T   G   T   S   S   D   V   G   G   Y   N   Y   V   S   W   Y   Q   Q   H   P

541/181                                          571/191
GGC AAA GCC CCC AAA CTC ATG ATT TAT GAG GGC AGT AAG CGG CCC TCA GGG GTT TCT AAT
 G   K   A   P   K   L   M   I   Y   E   G   S   K   R   P   S   G   V   S   N

601/201                                          631/211
CGC TTC TCT GGC TCC AAG TCT GGC AAC ACG GCC TCC CTG ACA ATC TCT GGG CTC CAG GCT
 R   F   S   G   S   K   S   G   N   T   A   S   L   T   I   S   G   L   Q   A

661/221                                          691/231
GAG GAC GAG GCT GAT TAT TAC TGC AGC TCA TAT ACA ACC AGG AGC ACT CGA GTT TTC GGC
 E   D   E   A   D   Y   Y   C   S   S   Y   T   T   R   S   T   R   V   F   G

721/241
GGA GGG ACC AAG CTG ACC GTC CTA GGT
 G   G   T   K   L   T   V   L   G
```

Experimental Part

Isolation of Antibody Fragments Against the 'Long' TN-C Isoform

A phage display library of human scFv was selected using, as an antigen, the 'long' TN-C variant including all FNIII domains subjected to alternative splicing. Culture media of bacterial colonies obtained from said selection were analysed by the ELISA technique using, as antigens, TN-C variants with all FNIII domains ('long') or with no FNIII domain ('short') subjected to alternative splicing.

This investigation allowed the identification of a clone producing specific antibodies for the TN-C 'long' form. From the supernatant of the bacterial culture of said clone, denominated TN11, scFv was purified by column immunochromatography on Sepharose conjugated with recombinant fragment A-D (containing all FNIII domains subjected to alternative splicing).

Figure 1:
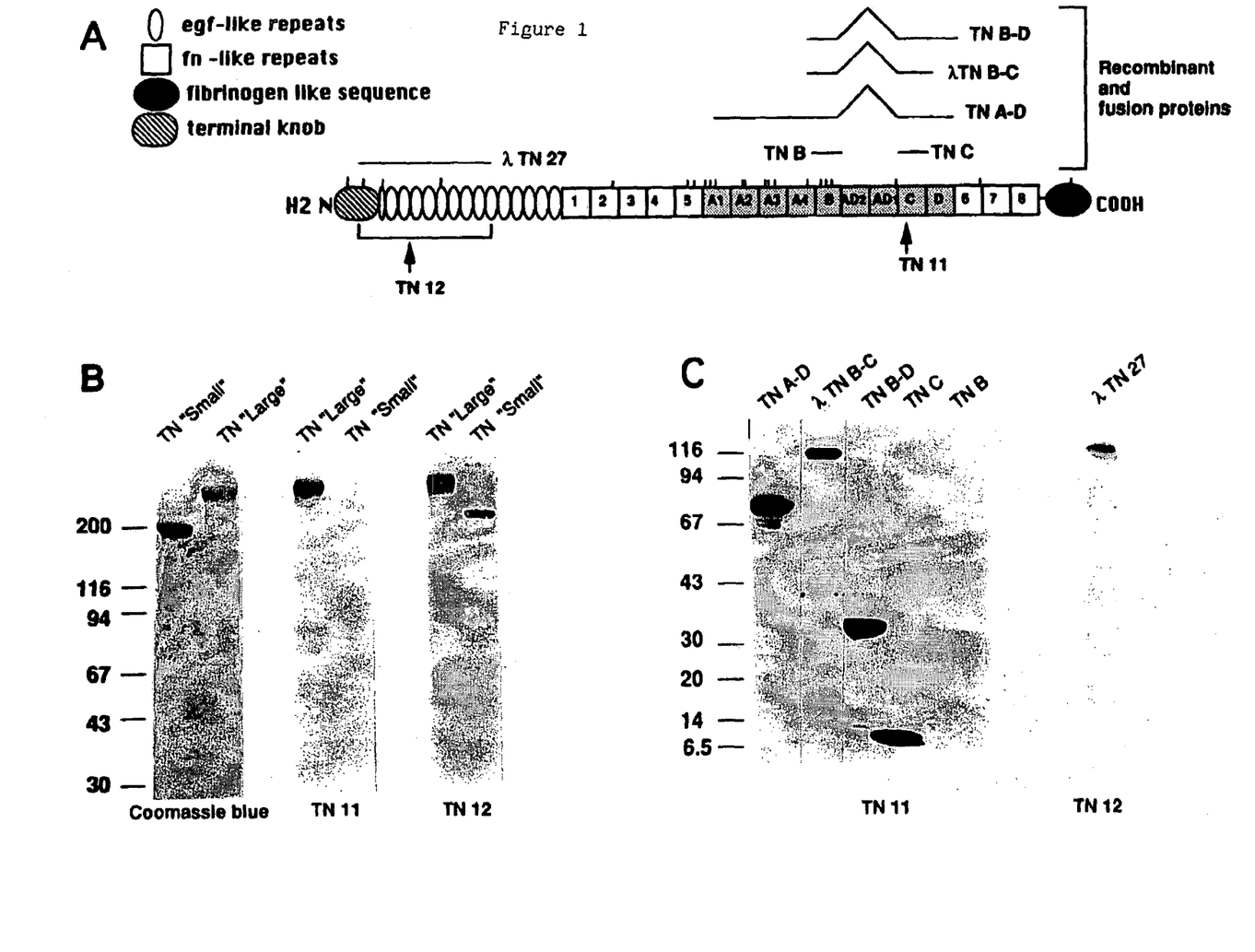

TN11 was further characterised by the immunoblotting technique, which allowed the evaluation of the specific reaction with 'long' and 'short' TN-Cs and with various recombinant and fusion proteins (TN A-D, TN B-D, TN C, TN B, λTN27 and λTNBC) containing various domains of human TN-C (FIG. 1 A). Said technique provided evidence that TN 11 not only recognised the TN-C 'long' form (as already found by the ELISA technique during selection phases), but also reacted specifically with all proteic fragments containing domain C (FIG. 1 B, C). This was a proof that the epitope recognised by TN11 is located inside domain C of TN-C. Similar investigations proved that TN11 does not react with the TN-C purified from the culture medium of normal human fibroblasts, because the TN-C produced by said cells does not contain domain C.

RT-PCR experiments were conducted on total RNA extracted from cultures of normal human fibroblasts (GM-6114, ATCC, Rockville, Md., USA), from cells derived from human melanoma (SKMEL-28, ATCC, Rockville, Md., USA) and from tissue samples of human glioblastoma and meningioma, using the following primers:

5' GCTACCCCCTAGTACTGATTTTATTGTCTA (from base. 4542 to 4571 of human TN-C sequence) (SEQ ID NO. 3), 5' TTTCCAGTGGCTCAGACTGC (complementary sequence, from base 5028 to base 5047) (SEQ ID NO. 4), 5'CTGGTCTGAGTCTTGGTTCCGTCC (complementary sequence, from base 5322 to base 5345) (SEQ ID NO. 5).

RT-PCR experiments evidenced that domain C of TN-C, which is absent in cells GM-6114 and SKMEL-28 as well as in meningiomas, is present in the mRNA of TN-C, purified from human glioblastoma fragments.

Figure 2:
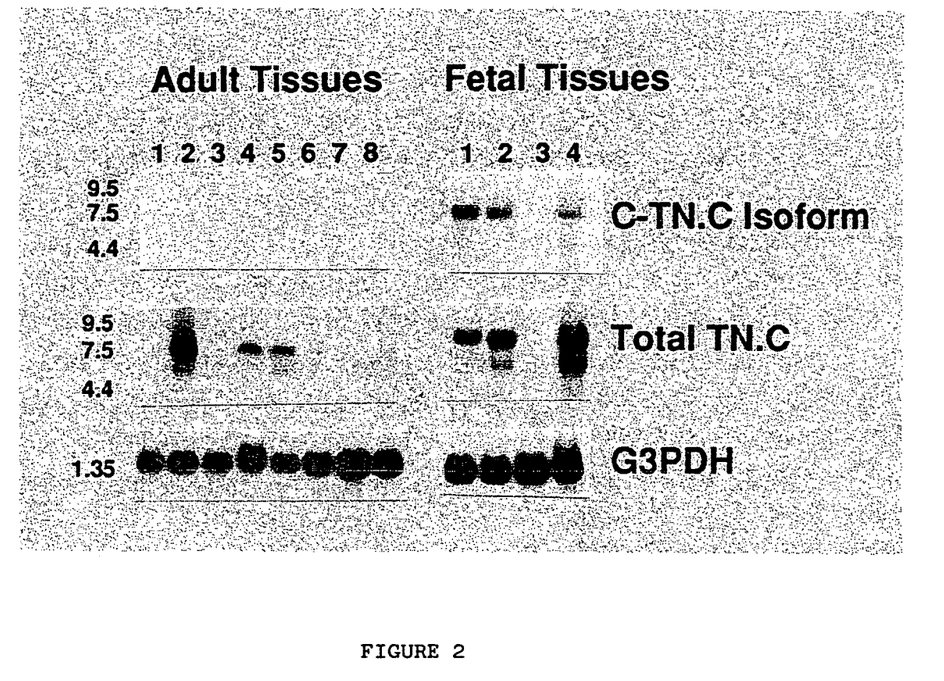
FIG. 2: Northern blots of poly(A)-rich RNA obtained from adult human tissues of (1) heart, (2) brain, (3) placenta, (4) lung, (5) liver, (6) skeletal muscle, (7) kidney, and (8) pancreas, and from fetal human tissues of (1) brain, (2) lung, (3) liver and (4) kidney, obtained using the cDNA probe described in the text, which is specific for the cTN-C isoform, the HT11 probe recognising all TN-C isoforms, and the cDNA of human G3PDH for blots normalisation. Numbers on the left represent measurements of standards (in kb).

Northern blotting analyses conducted using mRNA from normal human tissues, adult and embryonic respectively, and a cDNA probe containing 270 bases (4630 to 4899) of the human TN-C sequence, demonstrated that the mRNA of this domain is expressed only in fetal tissues (brain, liver, kidney) and is absent in the mRNA of adult tissues (FIG. 2).

Binding bond affinity of purified antibody TN 11 to 'long' TN was determined by interaction analysis using BIAcore. The dissociation constant was found to be 1.3×10−10.

The immunohistochemical analysis conducted using TN11, which is specific for domain C of TN-C, confirmed that domain C cannot be found in normal adult tissues. Conversely, there is a large presence of total TN-C (evidenced by the reaction with monoclonal antibody BC-4, specific for all human TN-C isoforms, since it recognises an epitope of the human TN-C molecule constant zone.

Figure 3:
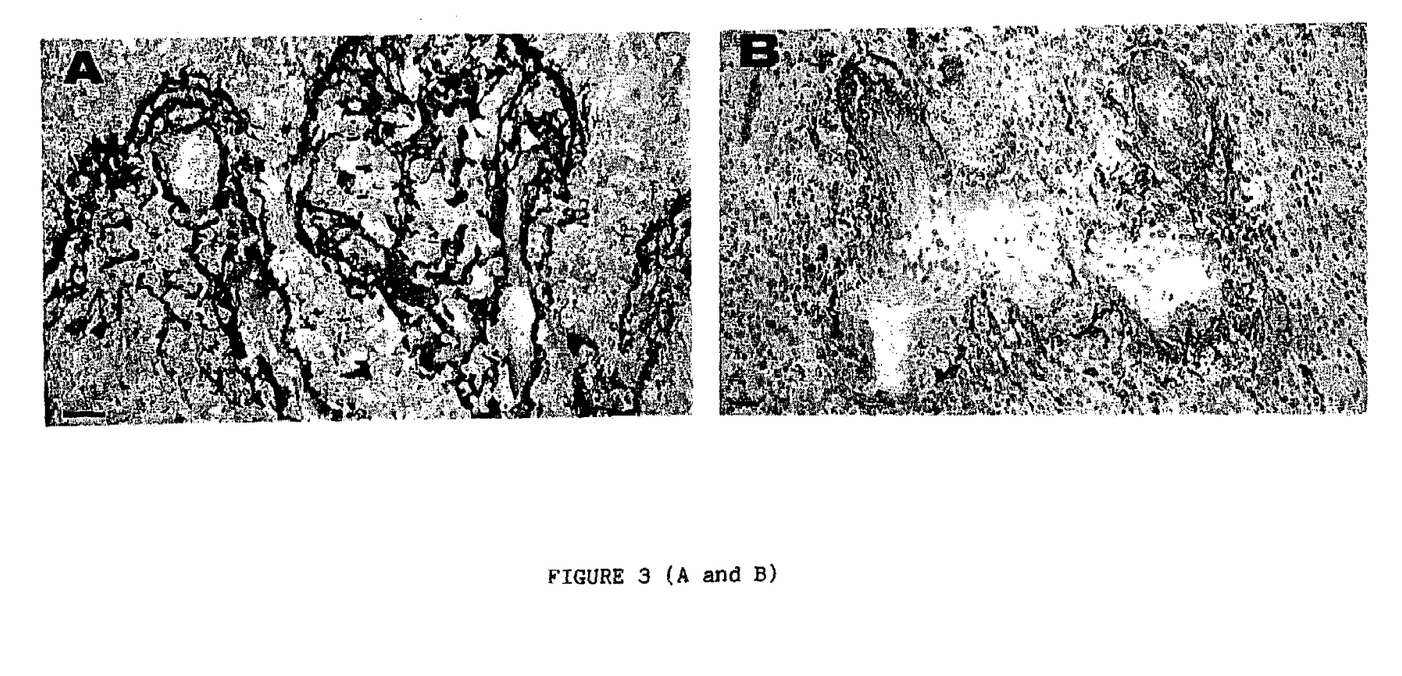
FIG. 3: Immunohistochemical analysis of glioblastoma sections with scFv TN11 (A and B) and with double staining obtained with scFv TN11 (red) and mAb KI67 (brown) (C, E, F, and G); section of cerebral metastasis of pulmonary carcinoma stained with scFv TN11 (D). Bar=10μ.
Figure 4:
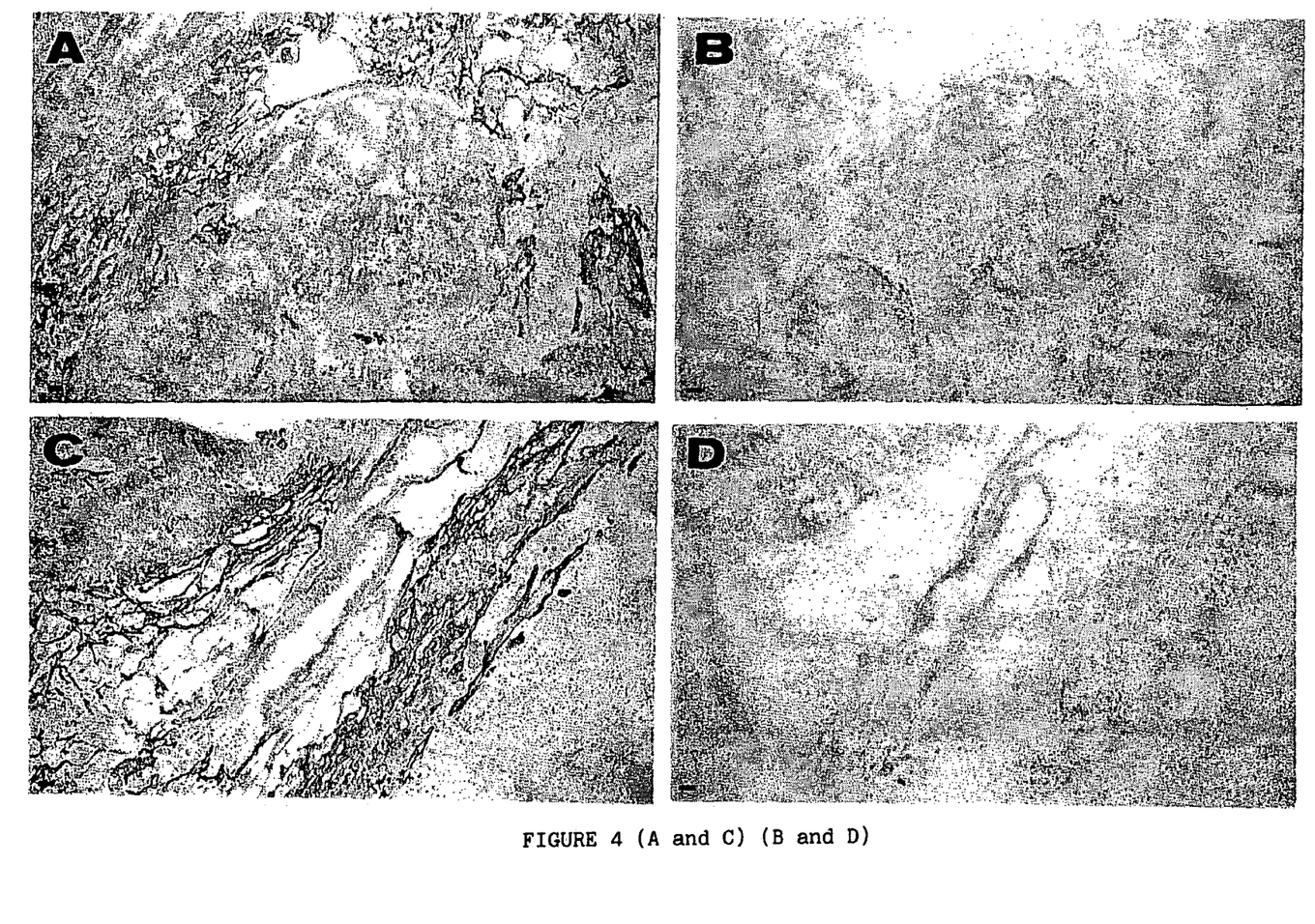
FIG. 4: Immunohistochemical analysis of serial sections of invasive ductal carcinoma of the breast using scFv TN12 (A and C) and scFv TN11 (B and D) and serial sections of meningioma stained with scFv TN12 (E) and scFv TN11 (F). Bar=10μ.

It was also found that almost all glioblastomas investigated express very high levels of domain C, with 14 cases of tumour out of the 15 highly positive ones (Table 2 and FIG. 3). In particular, the presence of this TN-C isoform was mainly identified in proximity of vascular structures in areas with high cellular proliferation activity, in the stroma of tumour cell nests (FIGS. 3 A, B, C, E, and G), and in proliferating cells (FIG. 3 F). Conversely, no positive reaction was obtained in other tumours of the brain, excepting 2 meningiomas out of the 23 that were weakly positive in proximity of vascular structures only (Table 2 and FIG. 4).

A large presence of cTN-C in pulmonary neoplasm sections, especially in proximity of vascular structures, was also observed.

Figure 5:
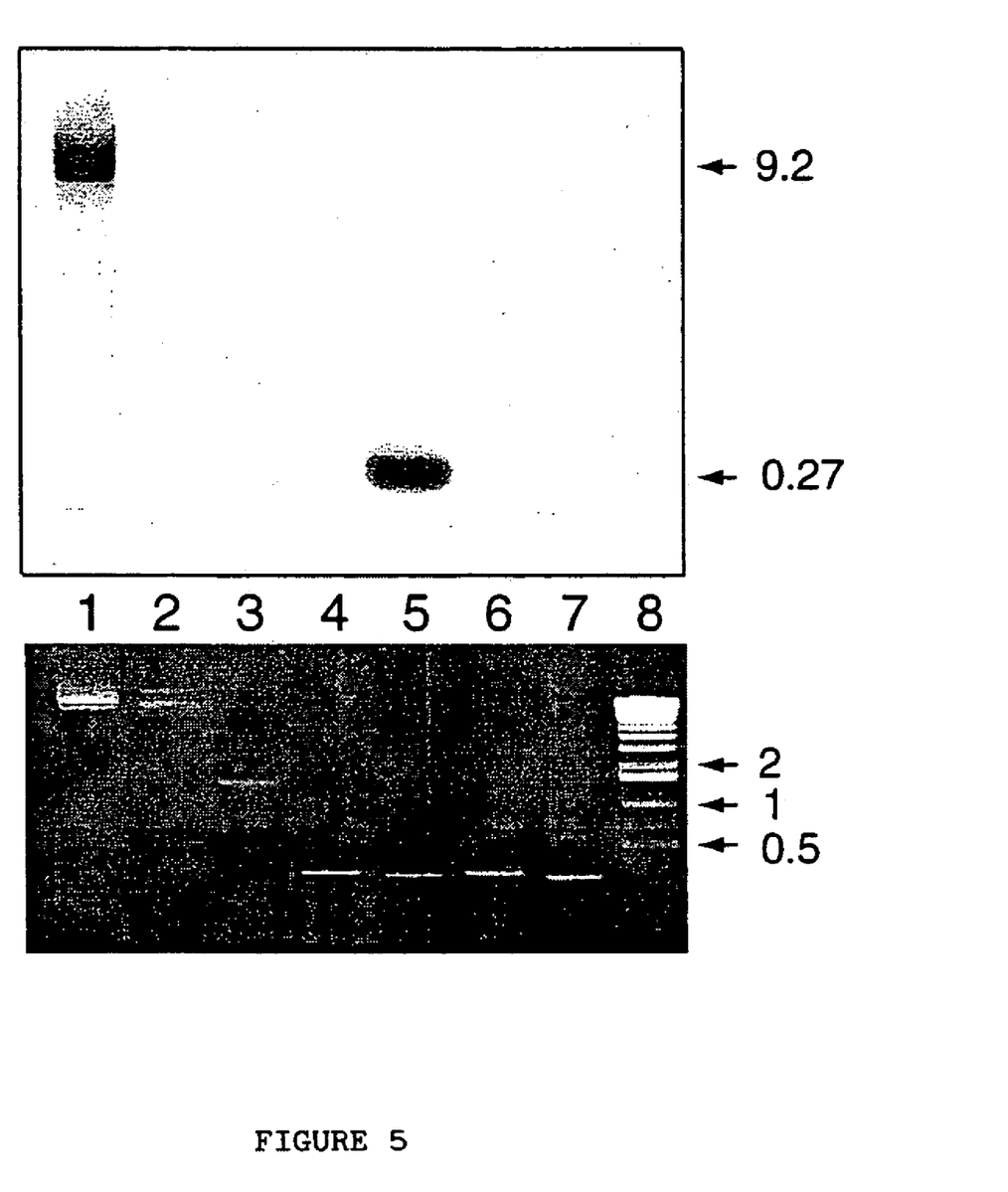
Figure 6:
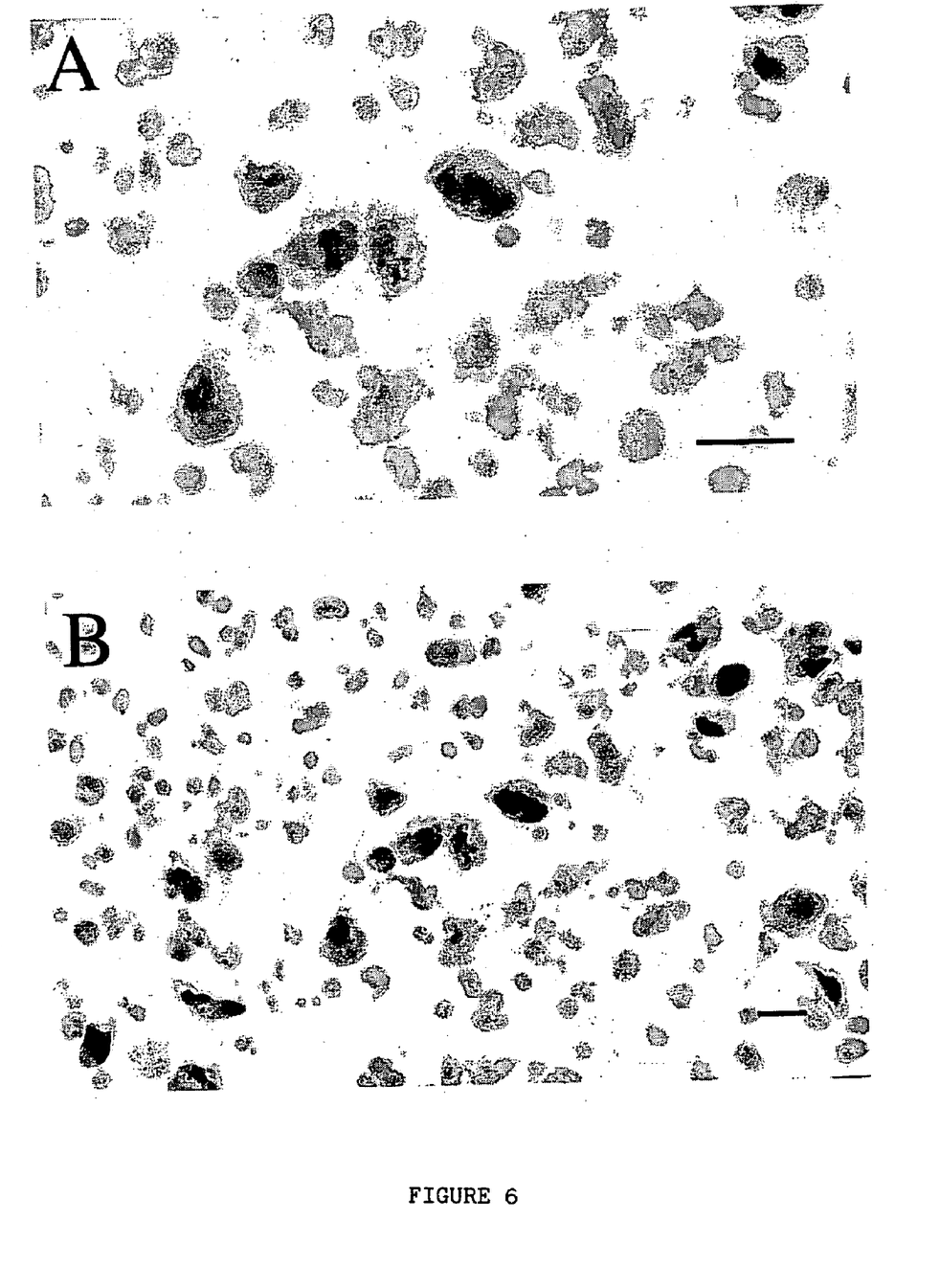
FIG. 6: Two magnifications of in situ hybridisation experiments on human glioblastoma cryostat sections, using the DIG-labelled cRNA probe of domain C. The positive signal is visible only in some tumour cells having large nucleus.

In situ hybridisations of glioblastoma cryostat sections (FIGS. 6 A and B) were conducted using DIG-labelled cRNA probes, specific for cTN-C (FIG. 5). The results obtained prove that the cTN-C isoform is produced by tumour cells, but not by all tumour cells.

cTN-C expression in vascular structures was also demonstrated in an experimental model of human melanoma, in nude mice (using SK-MEL-28 cells). Human-melanoma-carrier nude mice were injected with radio-labelled scFv TN11, which proved the antibody specific accumulation in tumour vascular structures only.

To conclude, the determination of the presence of the cTN-C isoform of TN-C is a valid method for the diagnosis of various types of tumours. Furthermore, the presence of said isoform in neoplastic tissues may be useful also for therapeutic purposes.

TABLE 2

Reactivity of scFv TN11 and TN12 with primary tumours of different histotype

| Tumour | | No. of positive/No. of tested cases | |
|---|---|---|---|
| | | TN11 | TN12 |
| Glioblastoma and anaplastic astrocytoma | | 15/16 | 16/16 |
| Astrocytoma Grade II | | 0/5 | 5/5 |
| Pilocytac astrocytoma | | 0/2 | 2/2 |
| Neurinoma | | 1/1 | 1/1 |
| Ependymoma | | 0/1 | 1/1 |
| Oligodendroglioma | (1) | 1/2 | 2/2 |
| Meningioma | (2) | 1/23 | 23/23 |
| Cerebral metastasis | (3) | 7/15 | 15/15 |
| Breast adenocarcinoma | (4) | 3/27 | 27/27 |
| Stomach adenocarcinoma | | 0/2 | 2/2 |
| Lung carcinoma | | 19/24 | 24/24 |

All tumours were highly positive with scFv TN12, which identifies all TN-C isoforms. scFv TN11 identifies the TN-C isoform containing domain C only.
(1) The positive case exhibited positivity only in some vascular structures.
(2) The positive case was a transition meningioma and exhibited positivity only in some vascular structures.
(3) Out of the 7 positive cases, 3 exhibited positivity in the connective tissue and in some vascular structures, and 3 exhibited positivity in some vascular structures only.
(4) In 3 positive cases, staining could be slightly evidenced.

All tumours were highly positive with scFv TN12, which identifies all TN-C isoforms. scFv TN11 identifies the TN-C isoform containing domain C only.

(1) The positive case exhibited positivity only in some vascular structures.

(2) The positive case was a transition meningioma and exhibited positivity only in some vascular structures.

(3) Out of the 7 positive cases, 3 exhibited positivity in the connective tissue and in some vascular structures, and 3 exhibited positivity in some vascular structures only.

(4) In 3 positive cases, staining could be slightly evidenced.

The invention claimed is:

1. A monoclonal antibody or antigen binding fragment thereof capable of identifying the human TN-C isoforms containing domain C (cTN-C) wherein said antibody or antigen binding fragment thereof binds to domain C in isoforms of TN-C expressed in cancer cells and/or vascular structures of malignant tumors and not to isofoms of TN-C expressed in normal adult human tissue.

2. The antibody or antigen binding fragment thereof as claimed in claim 1, wherein said antigen binding fragment is scFv, or an scFv fragment.

3. The antigen binding fragment as claimed in claim 2 wherein said antigen binding fragment has the amino acid sequence of SEQ ID NO. 1.

4. A diagnostic reagent comprising a conjugate consisting of a monoclonal antibody as claimed in claim 1 and a molecule selected from the group consisting of radioisotopes, fluorescent substances, and photosensitizers, allowing its use for diagnostic purposes.

5. A method for the preparation a reagent diagnostic for malignancy/cancer for the determination of cTN-C isoforms of TN-C in tissues and/or biological fluids comprising admixing the antibody or the antigen binding fragment thereof of claim 1 with a pharmaceutically acceptable carrier.

6. A method for the preparation of a reagent for diagnosing malignancy/cancer comprising admixing the diagnostic reagent of claim 4 with a pharmaceutically acceptable carrier wherein said diagnosing identifies cTN-C in tissues and or biological fluids by the binding of said diagnostic reagent to said cTN-C.

7. A method for the preparation of a composition comprising the antibody or antigen binding fragment thereof of claim 1 comprising admixing said antibody or antigen binding fragment thereof with a pharmaceutically acceptable carrier.

8. A conjugate consisting of a monoclonal antibody or an antigen binding fragment thereof as claimed in claim 1 and a molecule selected from the group consisting of radioisotopes, fluorescent substances, and photosensitizers allowing its use for diagnostic purposes.

9. A conjugate consisting of a monoclonal antibody or an antigen binding fragment thereof as claimed in claim 2 and a molecule selected from the group consisting of radioisotopes, fluorescent substances, and photosensitizers allowing its use for diagnostic purposes.

10. A conjugate consisting of a monoclonal antibody or an antigen binding fragment thereof as claimed in claim 3 and a molecule selected from the group consisting of radioisotopes, fluorescent substances, and photosensitizers, allowing its use for diagnostic purposes.

11. A method for the preparation of a reagent for diagnosing malignancy/cancer comprising admixing the conjugate of claim 9 with a pharmaceutically acceptable carrier wherein the diagnosing identifies cTN-C in tissues and/or biological fluids by the binding of said diagnostic reagent to said cTN-C.

12. A method for the preparation of a diagnostic reagent for diagnosing malignancy/cancer comprising admixing the conjugate of claim 10 with a pharmaceutically acceptable carrier wherein the diagnosing identifies cTN-C in tissues and/or biological fluids by the binding of said diagnostic reagent to said cTN-C.

* * * * *

SEQUENCE LISTING

<160> NUMBER OF SEQ ID NOS: 5

<210> SEQ ID NO 1
<211> LENGTH: 747
<212> TYPE: DNA
<213> ORGANISM: Homo Sapiens
<220> FEATURE:
<221> NAME/KEY: CDS
<222> LOCATION: (1)..(747)
<223> OTHER INFORMATION:

<400> SEQUENCE: 1

```
cag gtg cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
                20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
            35                  40                  45 gga ggg atc atc cct atc ttt ggt aca gca aac tac gca cag aag ttc     192
Gly Gly Ile Ile Pro Ile Phe Gly Thr Ala Asn Tyr Ala Gln Lys Phe
        50                  55                  60 cag ggc aga gtc acg att acc gcg gac gaa tcc acg agc aca gcc tac     240
Gln Gly Arg Val Thr Ile Thr Ala Asp Glu Ser Thr Ser Thr Ala Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga tcg aga cgt att acg att ttt gga gga ggt gct ttc gat atc     336
Ala Arg Ser Arg Arg Ile Thr Ile Phe Gly Gly Gly Ala Phe Asp Ile
                100                 105                 110 tgg ggc cga ggc acc atg gtc acc gtc tct tca ggt ggg ggc ggt tca     384
Trp Gly Arg Gly Thr Met Val Thr Val Ser Ser Gly Gly Gly Gly Ser
            115                 120                 125 ggc gga ggt ggc agc ggc ggt ggc gga tcg cag tcc gtg ctg act cag     432
Gly Gly Gly Gly Ser Gly Gly Gly Gly Ser Gln Ser Val Leu Thr Gln
        130                 135                 140 cct gcc tcc gtg tct ggg tct cct gga cag tcg atc acc atc tcc tgc     480
Pro Ala Ser Val Ser Gly Ser Pro Gly Gln Ser Ile Thr Ile Ser Cys
145                 150                 155                 160 act gga acc agc agt gat gtt ggt ggt tat aac tat gtc tcc tgg tac     528
Thr Gly Thr Ser Ser Asp Val Gly Gly Tyr Asn Tyr Val Ser Trp Tyr
                165                 170                 175 caa caa cac cca ggc aaa gcc ccc aaa ctc atg att tat gag ggc agt     576
Gln Gln His Pro Gly Lys Ala Pro Lys Leu Met Ile Tyr Glu Gly Ser
                180                 185                 190 aag cgg ccc tca ggg gtt tct aat cgc ttc tct ggc tcc aag tct ggc     624
Lys Arg Pro Ser Gly Val Ser Asn Arg Phe Ser Gly Ser Lys Ser Gly
            195                 200                 205 aac acg gcc tcc ctg aca atc tct ggg ctc cag gct gag gac gag gct     672
Asn Thr Ala Ser Leu Thr Ile Ser Gly Leu Gln Ala Glu Asp Glu Ala
        210                 215                 220 gat tat tac tgc agc tca tat aca acc agg agc act cga gtt ttc ggc     720
Asp Tyr Tyr Cys Ser Ser Tyr Thr Thr Arg Ser Thr Arg Val Phe Gly
225                 230                 235                 240 gga ggg acc aag ctg acc gtc cta ggt                                  747
Gly Gly Thr Lys Leu Thr Val Leu Gly
                245
```

<210> SEQ ID NO 2
<211> LENGTH: 249
<212> TYPE: PRT
<213> ORGANISM: Homo Sapiens

<400> SEQUENCE: 2

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Arg Ile Thr Ile Phe Gly Gly Ala Phe Asp Ile
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Ser Gln Ser Val Leu Thr Gln
    130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Gly Ser
            180                 185                 190

Lys Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Thr Arg Ser Thr Arg Val Phe Gly
225                 230                 235                 240

Gly Gly Thr Lys Leu Thr Val Leu Gly
                245
```

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3 gctacccct agtactgatt ttattgtcta                                    30

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4

```
-continued tttccagtgg ctcagactgc                                          20

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
ctggtctgag tcttggttcc gtcc                                     24
```